Figure 1:
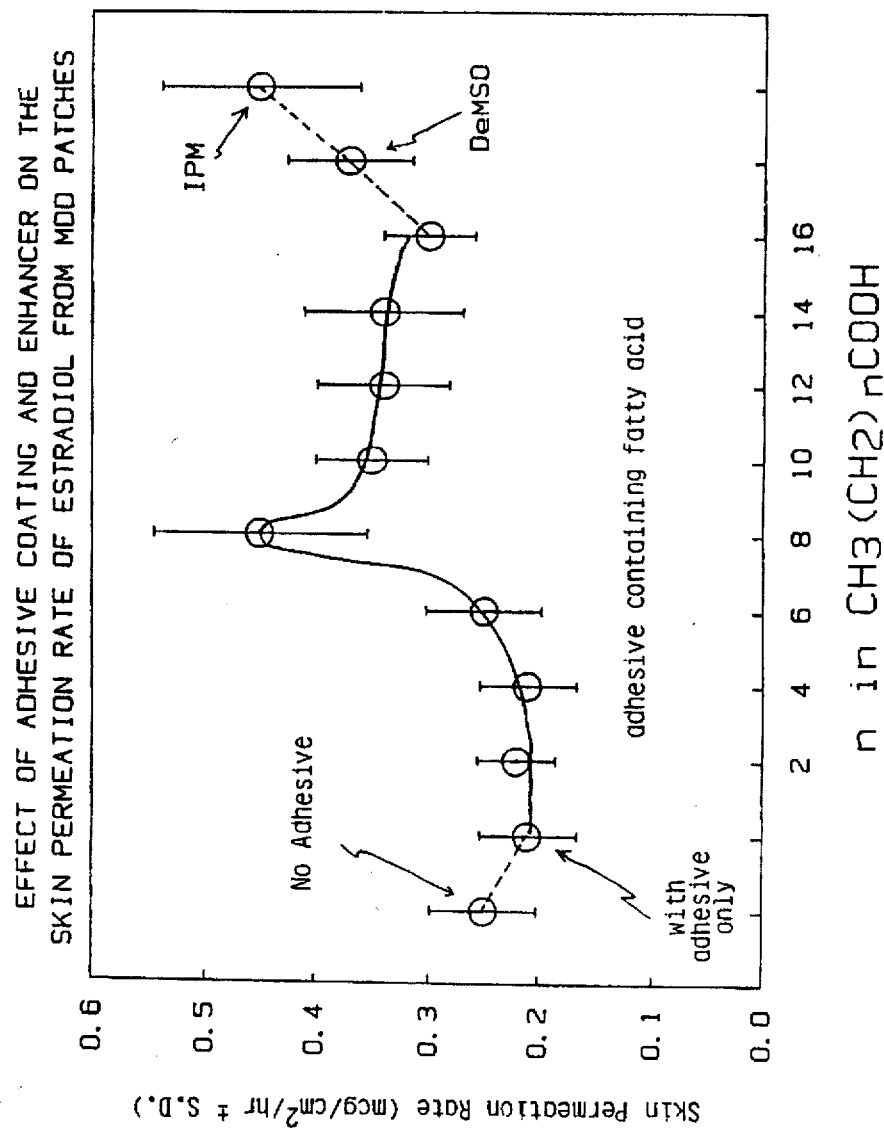

United States Patent [19]

Chien et al.

[11] Patent Number: 4,818,540
[45] Date of Patent: Apr. 4, 1989

[54] TRANSDERMAL FERTILITY CONTROL SYSTEM AND PROCESS

[75] Inventors: Yie W. Chien, North Brunswick; Te-Yen Chien; Yih-Chain Huang, both of Piscataway, all of N.J.

[73] Assignee: Rutgers, The State University of New Jersey, New Brunswick, N.J.

[21] Appl. No.: 902,440

[22] Filed: Aug. 29, 1986

Related U.S. Application Data

[63] Continuation-in-part of Ser. No. 705,194, Feb. 25, 1985, and a continuation-in-part of Ser. No. 770,968, Aug. 30, 1985.

[51] Int. Cl.$^4$ .............................................. A61F 13/00
[52] U.S. Cl. ...................................... 424/448; 424/449
[58] Field of Search ............................. 424/448, 449

[56] References Cited

U.S. PATENT DOCUMENTS

| 4,336,243 | 6/1982 | Sanvordecker | 424/449 |
| 4,615,699 | 10/1986 | Gale et al. | 424/449 |
| 4,624,665 | 11/1986 | Nuwayser | 424/449 |
| 4,687,481 | 8/1987 | Nuwayser | 424/449 |

*Primary Examiner*—Thurman K. Page
*Assistant Examiner*—L. R. Horne
*Attorney, Agent, or Firm*—Leroy G. Sinn

[57] ABSTRACT

Transdermal fertility-controlling absorption polymer matrix dosage units have been developed which comprise a backing layer, an adjoining layer of a solid polymer matrix in which minimum effective daily doses of an estrogen and a progestin are microdispersed and released for transdermal absorption. Presently preferred is use of the natural estrogen, 17-beta-estradiol, and of the progestin, levonorgestrel. The units have a biologically acceptable adhesive polymer layer. The polymer matrix as well as the adhesive layer can have dispersed one or more skin permeation enhancers. Dosage units are provided which transdermally deliver at least minimum daily doses of the estrogen and progestin for multiple days, such as for one week. The invention also provides a process of fertility control using the novel polymer matrix dosage units for the first three weeks of consecutive menstrual cycles of the subject desiring fertility control.

30 Claims, 4 Drawing Sheets

TRANSDERMAL FERTILITY CONTROL SYSTEM AND PROCESS

This invention was made with Government support under the National Institute of Child Health and Human Development, Grant No. N01-HD-5-2912, and the Government has a right to a license to the invention.

CROSS-REFERENCE TO RELATED APPLICATIONS

This application is continuation-in-part of both U.S. application Ser. No. 06/704,194, filed Feb. 25, 1985, by Yie W. Chien and Chia-Shun Lee and U.S. application Ser. No. 06/770,968, filed Aug. 30, 1985, by Yie W. Chien and Chia-Shun Lee.

This invention relates to a novel transdermal fertility control system and a process for controlling fertility. The system involves transdermal absorption dosage units adapted for adhesion to the female subject desiring fertility control or prevention of an unwanted pregnancy. Additionally, the invention relates to a method of controlling fertility by utilizrng a transdermal system of applying a series of transdermal polymer matrix dosage units having microdispersed in the matrix layer effective dosage amounts of an estrogen, preferably 17-beta-estradiol and a progestin, preferably levonorgestrel.

BACKGROUND ART

Fertility has been controlled by use of a number of orally administered hormone products. The products are ordinarily a combination of an estrogen and a progestin. A synthetic estrogen is ordinarily used as the estrogen component since the natural estrogen, 17-beta-estradiol, is almost completely destroyed, usually over 90 percent, when taken orally. It is destroyed to a degree in the digestive tract be tore it is absorbed but primarily the destructive metabolism of 17-beta-estradiol occurs during the "first pass" hepatic metabolism. Since such a large amount is destroyed, in order to provide an effective dosage orally, a large excess must be administered with uncertain effectiveness and a large amount of unwanted metabolic products. Therefore, a synthetic estrogen such as ethinyl estradiol normally is administered with less than desired results.

The progestin component generally inhibits, as intended, ovulation. Also, in the case of administered progestin, a substantial amount of metabolic breakdown occurs causing undesired metabolic products with undesired effects.

Therefore, in the oral administration of what is commonly referred to as "the pill" or other orally administered products, considerably overdosing is necessary to obtain a high degree of assurance that the desired fertility control will be obtained.

A number of major side effects have reportedly been associated with the administration of oral fertility control preparations, like thrombophlebitis and thrombosis, pulmonary embolism, coronary thrombosis, myocardial infarction, cerebral thrombosis, cerebral hemorrhage and hypertension. These side effects have been attributed to the estrogen component in the oral preparations. Use of the progestinonly preparations (mini-pill) has been found to eliminate the side effects of estrogen. However, the fertility control is less than that of the combined preparations and the menstrual cycle also becomes more irregular. It has been reported that less incidence of irregular bleeding is observed if the progestin is administered at a more constant rate of delivery. Besides the side effects, the oral fertility control preparations also have the disadvantage of fertility control efficacy depending highly on the degree of patient compliance. The risk of pregnancy is known to increase with each pill missed.

An ideal and patient-acceptable fertility control system should provide the following advantages: minimized side effect, increased ease of administration, rapid termination of treatment, if needed, and improved patient compliance. In recent years, considerable attention has already been directed to the development of implantable, intrauterine, intracervical or intravaginal fertility control delivery systems to provide a prolonged and controlled administration of steroidal hormones to the body for achieving fertility control; however, none of the delivery systems developed so far can be considered as ideal and side effect-free.

Other fertility control means have been used, such as topical creams and intravaginal devices, which deliver combinations of one or more progestins and one or more estrogens, including the naturally-occurring estrogen, 17-beta-estradiol. However, the undesirable aspects of such fertility control systems are evident.

It is, therefore, highly desired that transdermal systems be provided which permit (1) use of the natural estrogen, 17-beta-estradiol, (2) use of a minimum number of dosage units for each menstrual cycle, such as use of three successive weekly dosage units, (3) would adhere to the skin of the subject and provide sufficiently high levels of estrogen and progestin hormones to provide high assurance of fertility control without a high amount of undesired metabolic or chemical degradative products. Development of a ratecontrol transdermal drug delivery system, which is capable of minimizing any individual variability and regional differences in skin permeability, is a necessity to attain a predictable blood level of a drug. The transdermal ratecontrol drug administration is known to offer several potential advantages for systemic medication: (i) avoidance of the risk and inconvenience of intravenous therapy and of the variability in absorption and metabolism associated with oral therapy; (ii) continuity of drug administration, permitting the use of a pharmacologically-active agent with short biological half-life; (iii) efficacy can be achieved with lower total daily dosage of drug, because of reduced hepatic first-pass metabolism and continuous drug input; (iv) less chance of over- or under-dosing, as a result of prolonged, programmed delivery of drug at required therapeutic rate; (v) provision of a simplified medication regimen; and (vi) ability to rapidly terminate the drug infusion, if needed, by removal of the drug delivery system from skin surface. Therefore, a transdermal contraceptive delivery system, which is capable of providing dual-delivery of an estrogen and a progestin at controlled rates for a specific duration would be an ideal system for achieving fertility regulation in women.

SUMMARY OF INVENTION

Provided by this invention is a transdermal fertility control absorption system which permits fertility control by using sequentially three transdermal adhesive dosage units which can easily be applied to a selected skin area.

The first patch ordinarily is applied on the fifth day of a menstrual cycle. The dosage unit is replaced by the second unit after 7 days and the second is replaced by a third at the end of another 7 days. Then, at the beginning of the next menstrual cycle, another sequential course of 3 fertility control patches is again used, which course is repeated again and again as long as desired.

The transdermal fertility control dosage units of this invention comprise:

(a) a backing layer which is substantially impervious to the estrogen and progestin hormones to be delivered transdermally;

(b) a polymer matrix disc layer which is in contact with said backing layer and which has micro-dispersed therein an amount of estrogen and progestin hormone capable of transdermal absorption, said disc layer providing a dosage amount of the hormones to be delivered transdermally; and (c) an adhesive means which adheres the dosage unit in intimate contact with the skin of the subject being treated to permit the hormones to be absorbed transdermally.

The hormones microdispersed therein comprise an amount of 17-beta-estradiol or other desired estrogen effective in providing the role of estrogen in fertility control and an amount of levonorgestrel or other desired progestin which will provide the role of progestin in the desired fertility control system. Desirably, the dosage units will provide the desired rate of transdermal absorption of the estrogen and progestin components for a several day period, preferably for one week. Use of week-long transdermal dosage units minimize the possibility of missed administration of a dosage during the required fertility control period of days.

The backing layer is made from materials that are substantially impermeable with regard to the hormones of the transdermal dosage unit. It can be made of polymers such as polyethylene, polypropylene, polyurethane, polyvinylchloride, polyesters such as poly(ethylene phthalate), and foils such as laminates of polymer films with metallic foils such as aluminum foil.

The polymer matrix disc layer is suitably fabricated from biologically acceptable lipophilic polymers. The polymer matrix disc layer which has the hormones distributed therein can suitably be made of a medical-grade silicone polymer such as a polydimethylsiloxane polymer. The silicone polymer can also be a block or graft or other type copolymer. The hormones are suitably dispersed in the silicone polymer, to which mixture a curing agent is suitably added. The polymer-hormone mixture is then formed into a layer of an appropriate thickness and suitable surface area and is cured, if desired. The matrix layer is adhered to the backing layer. Other suitable polymers which can be used in the formulation of the polymer matrix disc layer are elastomers or thermoplastics. Care must be taken that the polymer selected is compatible with the pharmaceutical, permits its release for transdermal absorption and is free or sufficiently free from any biologically unacceptable components.

The estrogen hormone is preferably the naturally occurring estrogen: 17-beta-estradiol. Other estrogenic steroid hormones can be used in partial or complete replacement of 17-beta-estradiol. For example, an ester which is biologically compatible and can be absorbed effectively transdermally. Also, it is ordinarily desired that such esters are bioconvertible by components of the skin or other portions o i the body, such as hydrolytical enzymes (e.g., esterase), to 17-beta-estradiol or other desired estrogenic steroid. If the derivative is an ester, the derivative can be a mono- or di-ester if the estrogenic steroid has two esterifiable groups. In the case of estradiol, it has hydroxy groups at the 3- and 17-positions and, therefore, the 3-mono and 17-mono as well as the 3,17 di-esters can be made by generally known esterification methods. Some ester derivatives will be absorbed more readily than the basic 17-beta-estradiol or other estrogenic steroid, which is the basic compound. In selection of ester derivatives, it is ordinarily preferred that the main estrogen hormone used be absorbed at a rate to provide a desirable amount of the estrogen hormone component on a daily basis in a system which simultaneously effects transdermal absorption of the progestin hormone in an effective daily dosage amount over a several day period, preferably one week.

Valerate mono- and di-esters of estradiol are presently considered to be desirable esters. In formulating the polymer disc layer, it is desirable at times to utilize two or more estrogens, such as the combination of an estradiol ester, like estradiol valerate, with an amount of 17-beta-estradiol.

A presently preferred progestin is levonorgestrol. About 20 cg/day of progestin based on levonorgestrol and about 25 mcg/day of estrogen based on 17-beta-estradiol are presently believed desired daily doses for humans.

Finally, the adhesive means of the dosage unit is assembled with the other layer elements to form the dosage units. The adhesive means selected can vary depending on many factors including economic factors such as the type of manufacturing equipment most readily available, the rapidity of absorption desired or other factors. For example, the adhesive layer can be applied directly to the polymer matrix disc layer. A skin permeation enhancer compound can be mixed thoroughly with the adhesive polymer which is suitable for adhesion to the skin locus to which the transdermal matrix dosage unit will be applied. The adhesive polymer-skin permeation enhancer layer can be applied to the polymer matrix disc layer by spraying or by solvent casting or laminating. The concentration of skin permeation enhancer compound, if employed, can be reduced in the portion of the adhesive layer means, especially if less than desired adhesion is realized in the adhesive layer, by applying the surface portion of the adhesive layer, separately, wherein the adhesive composition has a lower concentration of skin permeation enhancer compound. The adhesive layer is desirably thin in the micron-range thickness, suitable 10–200 microns in thickness, desirably about 20 to 180 microns, and preferably about 30 to 150 microns in thickness. An effective amount of a skin permeation enhancer compound can also be incorporated into the hormone-containing disc layer. Also, if desired, the adhesive means can be in the form of a ring adhered to the backing layer which extends beyond the circumference of the disc layer. When such a concentric ring adhesive means is employed, the exposed surface of the hormone-containing disc layer is held in intimate contact wit the skin of the subject treated.

The absorption rate of the transdermal hormone absorption dosage units of the invention can be increased, such as by having an Enhancing Factor of at least 1.2, preferably at least 1.3, and more preferably at least about 1.5. Enhancing Factor is defined as the ratio of normalized permeation rate [in mcg/cm$^2$/hr] of a dosage unit of this invention with skin permeation enhancer/the normalized permeation rate of a corresponding dosage unit without enhancer.

The invention also is a process for administering said hormones transdermally by forming hormone-containing polymer matrix disc dosage unit having a polymer matrix disc layer which has the hormone dosages dispersed therein, to which matrix disc is adhered a backing layer, said dosage unit having assembled therewith an adhesive means to hold the dosage unit in intimate contact with the skin of the subject treated so that the hormones are absorbed transdermally, and by applying said dosage unit by way of said adhesive means to the skin of the subject to be treated, whereby said hormones are transdermally administered to said subject to achieve fertility control.

DESCRIPTION OF THE INVENTION AND THE PREFERRED EMBODIMENTS

The backing layer can be made of any suitable material which is impermeable to the hormones of the polymer matrix layer. The backing layer serves as a protective cover for the matrix layer and provides also a support function. The backing can be formed so that it is essentially the same size layer as the hormone-containing matrix disc layer or it can be of larger dimension so that it can extend beyond the side f the matrix disc layer or overlay the side or sides of the hormone-containing disc layer and then can extend outwardly in a manner that the surface of the extension of the backing layer can be the base for an adhesive means. For long-term applications, e.g., for seven days, it might be desirable to use microporous and/or breathable backing laminates, so hydration or maceration of the skin can be minimized. The adhesive means holds the dosage unit in intimate contact with the skin of the subject treated. Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like . Preferably, the materials used for the backing layer are laminates of such polymer films with a metal foil such as aluminum foil. In such laminates, a polymer film of the laminate will usually be in contact with the polymer matrix layer. The backing layer aan be any appropriate thickness which will provide the desired protective and support functions. A suitable thickness will be from about 10 to about 200 microns. Desirably, the thickness will be from about 20 to about 150 microns, and preferably be from about 30 to about 100 microns.

The polymer matrix layer can be made from silicone elastomers of the general polydimethylsiloxane structure, such as silicone polymers of the following general formula:

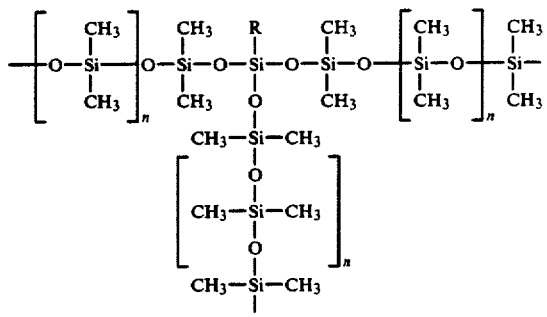

wherein R is alkyl or alkoxy containinl-7 carbon atoms, vinyl or phenyl and wherein n is about 100 to about 5000.

The silicone polymers selected preferably are cross-linkable at moderate temperatures, such as room temperature, using cross-linking catalysts which are biologically acceptable in the final polymer matrix and which are compatible with the hormone components to be used in making the polymer matrix dosage forms. Various suitable crosslinking agents can be used in crosslinking the above polymer, such as tetrapropoxy silane [Si(OCH$_2$ CH$_2$ CH$_3$)$_4$], if the silicone polymer has free hydroxy groups such as terminal hydroxy groups. A tin catalyst can be used for such crosslinking reaction. If a silicone polymer component has vinyl groups, it can be crosslinked with a dimethyl-silicone polymer using a catalyst such as a platinum catalyst. Some suitable silicone polymers are cross-linkable copolymers having dimethyl and methylvinyl siloxane units, which can be cross-linked as by using a suitable peroxide catalyst. Other cross-linking sites can be present in the polysiloxane elastomers used. Suitable silicone medical-grade polymers are sold unde the designations Silastic 382, Q7-4635, Q7-4650, Q7-4665, Q7-4735, Q7-4750, Q7-4765 and MDX-4-4210.

The silicone polymers selected can also have a "block" or "graft" structure or both. By "block" structure is meant that the polymer can have a section or block of the polymer chain structure of the polymer which can have a repeating unit of one type, such as dimethylsiloxane, and then have a succeeding block made up of repeating units of another type, such as methylvinylsiloxane, diphenylsiloxane, diisopropyl siloxane units or other siloxane or silane units or even of monomer units of a compatible non siloxane or non silane type. The blocks can vary in length and be repeated as desired. For example, if the blocks are represented as "A" and "B", respectively, the block copolymer can be A-B or A-B-A or A-B-A-B, etc. The "graft" structure simply means that to the main polymer chain, one or more polymer chains are attached. Those grafted chains can have the same polymer units as those of the main chain or can be different, as described above in connection with "block" copolymers. Also, the polymer used can be of a different type wherein copolymerizable monomers are placed together in a polymerization reactor so the main chain can have a certain population of each of the monomeric units.

The following are examples of block copolymers of the type which can be utilized in this invention.

"A" Block

-continued

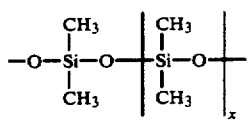

"B" Block $$-CH_2-CH_2-O+CH_2-CH_2-O+_z$$

or

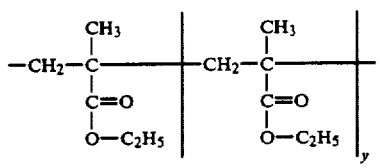

wherein y and z represent the number of repeating units sufficient to provide the desired property in the polymer, such as from about 10 to about 5000.

Generally, those polymers used to form the biologically acceptable polymer matrix are those capable of forming thin walls or coatings through which hormones can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix would affect the release rate of the hormones as well as the capability of the dosage unit to remain in place for convenience of removal.

Exemplary materials for fabricating the biologically acceptable polymer matrix include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylate, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylene-vinyloxyethanol copolymer; silicone copolymers, for example, polysiloxanepolycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like. For best results, the biologically acceptable polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after microdispersing the hormones into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

The adhesive means is suitably made in the form of a layer covering the hormone-containing disc and using a silicone adhesive, such as a polydimethylsiloxane adhesive depicted by the following formula:

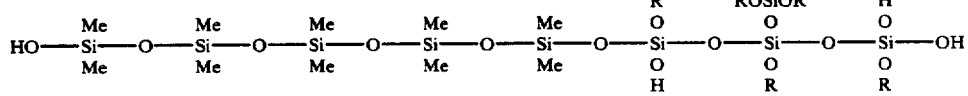

wherein Me is methyl and R is $Si(CH_3)_3$.

For example, adhesive products or amine-resistant adhesive products sold by Dow Corning, such as the one sold under the designation DC-355, are suitable for use in making the adhesive layer. The adhesive polymer must be biologically acceptable and compatible with the hormones and skin permeation enhancer, if used. Certain polyacrylic adhesive polymers (in the form of an alkyl ester, amide, free acid, or the like) or polyisobutylene adhesive polymers can also be used with some hormones. Other suitable hypoallergenic pressure-sensitive contact adhesive compositions can also be used. A preferred adhesive layer is pressure-sensitive.

However, depending upon economic and other factors, if desired, the adhesive means can be in the form of a ring attached, for example, to an extended portion of the backing layer so that the adhesive layer is adjacent to the sidewall of the hormone-containing disc layer. The width of such adjacent adhesive ring must be adequate to hold the dosage unit securely to the subject being treated. Ordinarily, a suitable width of such adhesive ring can be about 0.2 to about 1.2 cm, preferably about 0.3 to about 1.0 cm.

The adhesive means then is finally covered in with a releasable protective film layer which is made from materials which are substantially impermeable to the hormones, the skin permeation enhancer, if used, and any other components of the polymer matrix dosage unit. The polymer materials and metal foil laminates used for the backing layer may also be used to make the protective layer, provided the layer is made strippable or releasable such as by applying conventional siliconizing. A suitable releasable material for use with silicone polymer adhesive DC-355 is Scotchpak 1022 material sold by the 3M Company.

In making the hormone-containing polymer matrix disc layer, silicone elastomers such as polydimethylsiloxane of the formula described above can suitably be used. In making hormone-dispersed polymer matrix disc dosage units, it has been found suitable to use a polyol such as polyethylene glycol as a dispersing agent. Other suitable dispersing agents can also be used instead so long as they are effective. Water-soluble polyols are generally suitable. For example, polyethylene glycols, such as those having a molecular weight of about 400, can be used, the molecular weight being variable therefrom, such as suitably between 300 and 1500. Other suitable dispersing agents known to the formulating art can be used. Depending upon the hormones and the drug loading desired, a suitable amount of a dispersing agent can be varied from zero to about 50 percent (by weight) based o the weight of the polymer matrix disc. Commonly, the polyol is added as an aqueous solution with the polyol content varying from 10 to about 50 percent, based on the volume of the final aqueous solution. Aqueous solutions having about 40 percent polyol ordinarily are suitable, with some variation depending upon the rate of permeation desired, the particular hormones used, and at times, other factors. The hormones then are added to the polymer used to make the matrix disc layer. The amount of the hormones added depends upon the amount of hormone dosage and the duration of treatment desired in each dosage unit and the amount which can be incorporated into the polymer matrix disc to retain suitable structural, diffusion and other properties in the final matrix disc. It has been found, for example, that the hormones can be satisfactorily added to 70 parts of the polymer used in making the matrix disc, such as silicone elastomers. It has been found to be preferable to dissolve and disperse the hormones used in an amount of a selected aqueous solution of polyol, such as PEG 400. The mixture of the polymer and hormones or hormone-dispersing aqueous polyol solution is then thoroughly mixed using a high-torque mixer to form a homogeneous microdispersion of the hormones in the polymer. With continued agitation, an amount of cross-linking catalyst is desirably added together with a relatively low molecular weight polymer having a compatible chemical structure. For example, when polydimethylsiloxane based polymer is used as the polymer, a relatively low molecular weight polydimethylsiloxane and a cross-linking catalyst is added (such as 10 parts by weight of the low molecular weight polydimethylsiloxane and 30 drops of stannous octanoate per 100 g. amount of the final polydimethylsiloxane-hormone mixture) to the above illustrative composition of 20 parts of hormone dispersion and 70 parts or polydimethylsiloxane polymer. Again, the mixture is agitated with a high-torque mixer to form a uniform admixture. After each mixing step, the composition is subjected to vacuum to remove entrapped air.

The deaereated mixture is then placed in a device maker and neated to a suitable elevated temperature to promote cross-linking. A suitable temperature for cross-linking when the polymer used is polydimethylsiloxane of the above formula and the cross-linking catalyst is stannous octanoate, is from about 10° C. to about 200° C. desirably about 20° C. to about 100° C. The temperature used should not cause significant degradation of the hormones. The polymer matrix sheet desirably is about 0.05 to 5 mm, preferably about 0.1 to about 3 mm in thickness. The resulting cross-linked polymer matrix sheet is removed from the device maker and can be cut to form discs with desired shapes and sizes. The discs can be attached to a backing sheet, as prepared above, using an adhesive. The disc alternatively can be made directly on the backing sheet used. The discs generally should not exceed about 100 sq. cm in area, suitably about 5 to 100 sq. cm, preferably, about 8 to about 80 sq. cm, generally about 10 to 60 sq. cm being more preferable. The shape of the discs can vary; they can be circular, square, rectangular or other desired shape.

The hormone-containing polymer matrix disc layer, generally speaking, should contain some excess of the dispersed hormone over the dosage amount desired to be transdermally absorbed by the subject to be treated. Ordinarily, this excess is small, such as less than 2-fold excess. Generally speaking, an amount of the hormone used, which is sufficient, is less than 2 to about 10 times the desired dosage to about less than 2 to 5 times the desired dosage to be transdermally absorbed being adequate, depending upon the physiochemical properties of the hormones, as well as the nature of the polymer in the matrix disc layer and other factors.

The adhesive means, if it contains a skin permeation enhancer, is made as by dissolving the enhancer compound in a solvent ior the enhancer which is compatible with the adhesive polymer solution used to make the adhesive layer containing the skin permeation enhancer. Any suitable amount ot solvent can be used as necessary to dissolve the quantity of enhancer to be admixed with the adhesive polymer solution used. For example, 3 to 10 parts of solvent can be used to dissolve one part of skin permeation enhancer, depending upon the solubility of the enhancer. When using polydimethylsiloxane adhesive solution, it has been found suitable to use 2 to 20 parts of skin permeation enhancer in 20 to 50 parts of solvent (such as acetone, methyl ethyl ketone, trifluorotrichloroethane or other suitable solvent) and add the solution to 100 parts of the adhesive solution. The enhancer - adhesive combination is thoroughly mixed and a coating thereof is applied using a film coating machine, directly onto the polymer matrix or to a strippable release liner before laminating onto the polymer matrix, as described above. A suitable release liner is a poly(ethylene phthalate) laminated with aluminum foil or a Tefloncoated polyester film such as sold under the designation Scotchpak 1022. The poly(ethylene phthalate) side to which the adhesive-enhancer coating is applied, is made strippable by conventional siliconizing or by other suitable means. The thickness of the adhesive enhancer layer normally is suitable about 10 to about 200 microns, preferably about 30 to about 150 microns. The amount of enhancer in the adhesive layer depends in part on the rapidity at which it is desired that the hormones be absorbed. Generally speaking, about 1 to about 30 percent of skin permeation enhancer based on the weight of the adhesive is suitable, depending upon the enhancer, adhesive polymer, desired adhesiveness and other factors. Desirably, about 5 to about 20 percent of skin permeation enhancers are used depending upon the above recited factors. The adhesive layer containing the skin permeation enhancer is transferred to the polymer matrix disc surfaces by application of lamination technique under a constant pressure. Preferably, in order to assure adequate adhesion of the adhesive polymer layer to the skin of the subject treated, an enhancer-adhesive polymer solution having a relatively low concentration of enhancer, e.g., 1-2 percent based on the weight of the adhesive polymer is used to apply a coating to the release liner. The thickness of this coating ordinarily is a minor percentage of the thickness of the final adhesive layer, such as 20–40 percent or the total adhesive polymer layer. The remainder of the adhesive polymer layer having a suitable higher concentration of the enhancer is used to coat the matrix disc layer. Suitable higher concentrations of enhancer are usually 10 to about 30 percent based on the adhesive polymer weight, the solubility and desired final amount of skin enhancer agent and other factors. The solvent of the respective coatings is removed by evaporation. The respective coatings are combined to make the final adhesive polymer-enhancer agent layer by application of lamination technique under a constant pressure.

The four-layer transdermal hormone polymer matrix dosage units are excised. The backing layer, if desired, can be shaped around the sides of the dosage unit, including the polymer matrix layer, if such protection is desired. The resulting hormone polymer matrix dosage unit forms are then placed in appropriate packaging for storage until they are to be applied in transdermal treatment.

At least one estrogen and one progestin are dispersed in the polymer matrix disc layer. The specific hormones which may be dispersed in the polymer matrix disc layer include any hormones which are capable of being transdermally administered to a subject to be treated. With the controlled release of the hormone at a relatively steady rate over a prolonged period, typically several days and preferably one week, the subject is provided with the benefit of a steady infusion of the fertility-controlling amounts of hormones over a prolonged period. As examples of hormones which can be included in the polymer matrix disc layer of the present invention, there may be mentioned the following:

It is presently preferred to use 17-beta-estradiol. It is a natural hormone and ordinarily transdermally delivered by an adaptable system of this invention at a desirable daily rate while simultaneously a presently preferred progestin, the highly active levonorgestrel, is being transdermally absorbed at a desirably daily rate. 17-beta-estradiol and levonorgestrel are compatible and can be codispersed in the matrix layer-forming polymer. The transdermal dosage unit designed for one-week therapy is required to deliver at least about 20 mcg/20 cm$^2$/day of levonorgestrel (or an equivalent effective amount of another progestin) and 20–50 mcg/20 cm$^2$/day of 17-beta-estradiol (or an equivalent effective amount of another estrogen). That amount of progestin is believed to be necessary to inhibit ovulation and that amount of estrogen is believed needed to maintain normal female physiology and characteristics. Derivatives of 17-beta-estradiol which are biocompatible, capable of being absorbed transdermally and preferably bioconvertible to 17-beta-estradiol beta-estradiol can also be used, if the amount of absorption meets the required daily dose of the estrogen component and if the hormone components are compatible. Such derivatives of estradiol include esters, either mono- or di-esters. The monoesters can be either 3- or 17- esters. The estradiol esters can be, illustratively speaking, estradiol-3,17-diacetate; estradiol-3-acetate; estradiol-17-acetate; estradiol-3,17-divalerate; estradiol-3-valerate; estradiol-17-valerate; 3-mono, 17-mono and 3,17 dipivilate esters; 3-mono, 17-mono and 3,17-dipropionate esters; corresponding cypionate, heptanoate, benzoate and the like esters; ethinyl estradiol; estrone; and other estrogenic steroids and derivatives thereof which are transdermally absorbable.

Combinations of the above or other with estradiol, for example, a combination of estradiol and estradiol-17-valerate or further a combination of estradiol-17-valerate and estradiol-3,17-divalerate can be used with beneficial results. For example, 15–80% of each compound based on the total weight of the estrogenic steroid component can be used to obtain the desired result. Other combinations can also be used to obtain desired absorption and levels of 17-beta-estradiol in the body of the subject being treated.

It will be appreciated that the hormones may be added to the above mixture not only in the form of the pure chemical compound, but also in admixture with other pharmaceuticals which may be transdermally applied or with other ingredients which are not incompatible with the desired objective of transdermally administering the hormones to a patient. Thus, simple pharmacologically acceptable derivatives of the hormones such as ethers, esters, amides, acetals, salts and the like, if appropriate, may be used. In some cases, such derivatives may actually be preferred.

The progestin hormone, as expressed above, is preferably levonorgestrel. Levonorgestrel is a potent progestin on a weight-dose basis, which is an important factor since the progestins often show a lesser degree of transdermal absorption than shown by 17-beta-estradiol and certain derivatives thereof. Other progestins which can be used in part or total are norethindrone, norethynodrel and certain others. The progestin and estrogen hormones should have high compatibility with each other.

The progestin compound and the estrogenic steroid can ordinarily be compounded together in making the pharmaceutical dosage layer disc of this invention or can be microdispersed separately.

The skin permeation enhancers which can be used in carrying out this invention can vary. Ones that give preferred results with the polymer matrix dosage unit form having a specific hormone can vary. In some instances, the use of permeation enhancer in making a polymer matrix dosage form will result in good or even excellent absorption for one hormone, may result in no or relatively low enhancement when another hormone is used. Use of combinations of two or more of the skin permeation enhancer compounds frequently result in superior results, such as greater transdermal absorption.

Specific skin permeation enhancers which can be used in making the polymer matrix dosage forms of this invention include saturated and unsaturated fatty acids and their esters, alcohols, monoglycerides, acetate, diethanolamides and N, N-dimethylamides, such as oleic acid, propyl oleate, oleyl acetate, propyl myristate, myristyl alcohol, myristyl N, N dimethyl amide, stearic acid and stearyl alcohol, stearyl propyl ester, monostearin, and combinations of them with, for example, 1-dodecylazacycloheptan-2-one sold under the trademark Azone by Nelson Research and Development; decyl methyl sulfoxide, dimethyl sulfoxide, salicylic acid and derivatives, N,N-diethyl-m-toluamide, crotamiton, 1-substituted azacycloalkan-2-ones such as disclosed in U.S. Pat. No. 4,316,893 (the 1-substituent having 0–17 carbon atoms, preferably, 1–11 carbon atoms), and various other compounds which are biologically compatible and have transdermal permeation enhancement activity. Ethyl alcohol and other short chain alkanols (with 1–4 carbon atoms) which have substantially the same properties and activity as ethyl alcohol do not come within the definition of skin permeation enhancer as used herein.

The following examples are in illustration of the invention and are not intended to be limiting.

EXAMPLE 1

The following ingredients are used in making the hormone-containing polymer matrix discs: 17-beta-estradiol, 1 part; levonorgestrel, 2.5 parts; DC-360 polysiloxane medical fluid (20 cps), 12.4 parts; silicone (medical-grade) 382 elastomer (Silasti ® 382 elastomer, Dow Corning Corporation), 74.1 parts; 10 parts of 40 percent (V/V) PEG 400/water (W/W); catalyst M, 20 drops per 100 g. of the mixture.

The 17-beta-estradiol and levonorgestrel are thoroughly mixed in the PEG 400/water solution by using a high torque mixer (sold by Cole-Parmer Company) at about 1000 RPM, to form a mixture of paste-like consistency.

The hormone mixture is added to silicone (medical-grade) 382 elastomer and mixed well, using the high-torque mixer, to form a homogeneous hormone (PEG) polymer dispersion. The DC-360 polysiloxane medical fluid is added using the high torque mixer to the hormone-polymer mixture and 20 drops (for every 100 g of the mixture) of a cross-linking agent, which is designated as catalyst M and is stannous octanoate, are added to the hormone-microdispersed elastomer mixture. After each addition, the material is thoroughly mixed, and the dispersed mixture is placed under vacuum at 20 psi to remove entrapped air.

The hormone-polydimethylsil oxane dispersion is placed into a device maker and spread on a sheet of backing. A sheet of release liner is placed over the spread out mixture. The mixture is then cross-linked, using a pressure of 1000 psi at an elevated temperature (60° C.) for 30 minutes to form a cross-linked, medicated polymer sheet, which has a thickness of 0.2–3 mm.

The medicated polymer sheet is removed from the device maker and is cut into square discs having rounded corners of about 10 sq. cm. The discs are attached to a backing layer of heat sealable polyester film laminated to aluminum foil, which is sold by 3M Company as Scotchpak 1005 or 1006. The medicated discs are attached using an adhesive polymer solution, which is a silicone adhesive polymer sold by Dow Corning as DC-355.

The silicone adhesive is believed to have the following structure:

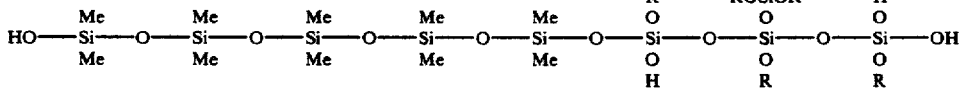

The skin permeation enhancer-adhesive film is made as by using the following ingredients: skin permeation enhancer, 6.5 parts; acetone 30 parts; and adhesive polymer solution, 100 parts. The skin permeation enhancer-adhesive layer is made by dissolving the 6.5 parts by weight of a skin permeation enhancer in 30 parts of acetone. The acetone solution then is added to 100 parts of a silicone adhesive solution sold by Dow-Corning under the designation DC-355.

The mixture is thoroughly mixed to form a homogeneous mixture of skin permeation enhancer and adhesive polymer, which is applied to a strip of a release liner which is a siliconized, or a Teflon-coated polyester film to permit easy removal of the release liner just prior to application of the final polymer matrix disc dosage unit to the subject to be transdermally treated. The adhesive mixture is applied at a controlled thickness. The formed layer has a thickness of about 50–200 microns. The layer is dried completely in vacuum to remove volatile matter.

The skin permeation enhancer-adhesive polymer layer with release liner is applied onto the hormone-containing polymer matrix disc with the attached backing layer under a constant pressure to provide a firmly adhered strip of a four-layered structure as follows:
1. Backing layer
2. Estradiol and levonorgestrel-containing polymer matrix layer
3. Skin permeation enhancer-adhesive layer
4. Release film layer which can be readily removed to permit application to the skin of the subject to receive transdermally the estradiol and levonorgestrel.

By use of an appropriate cutter, the strip is cut to provide the transdermal anti-fertility hormone polymer matrix dosage units which are square (with rounded corners) in shape and have an area of about 10 sq. cm.

The above polymer matrix disc dosage units can also be made to contain straight-chain saturated fatty acids (with alkyl chain length of $C_4$ to $C_{18}$), decyl methyl sulfoxide (DeMSO) or isopropyl myristate (IPM) or other skin permeation enhancers in the polymer matrix and/or in the adhesive layer.

The transdermal absorption of the hormones from the anti-fertility polymer matrix dosage units of this invention is evaluated by using a skin specimen from a "hairless" mouse or human cadaver by following the procedure described by P. R. Keshary and Y. W. Chien, in Drug Develop. & Ind. Pharm., 10 (6) 883–913 (1984).

Figure 2:
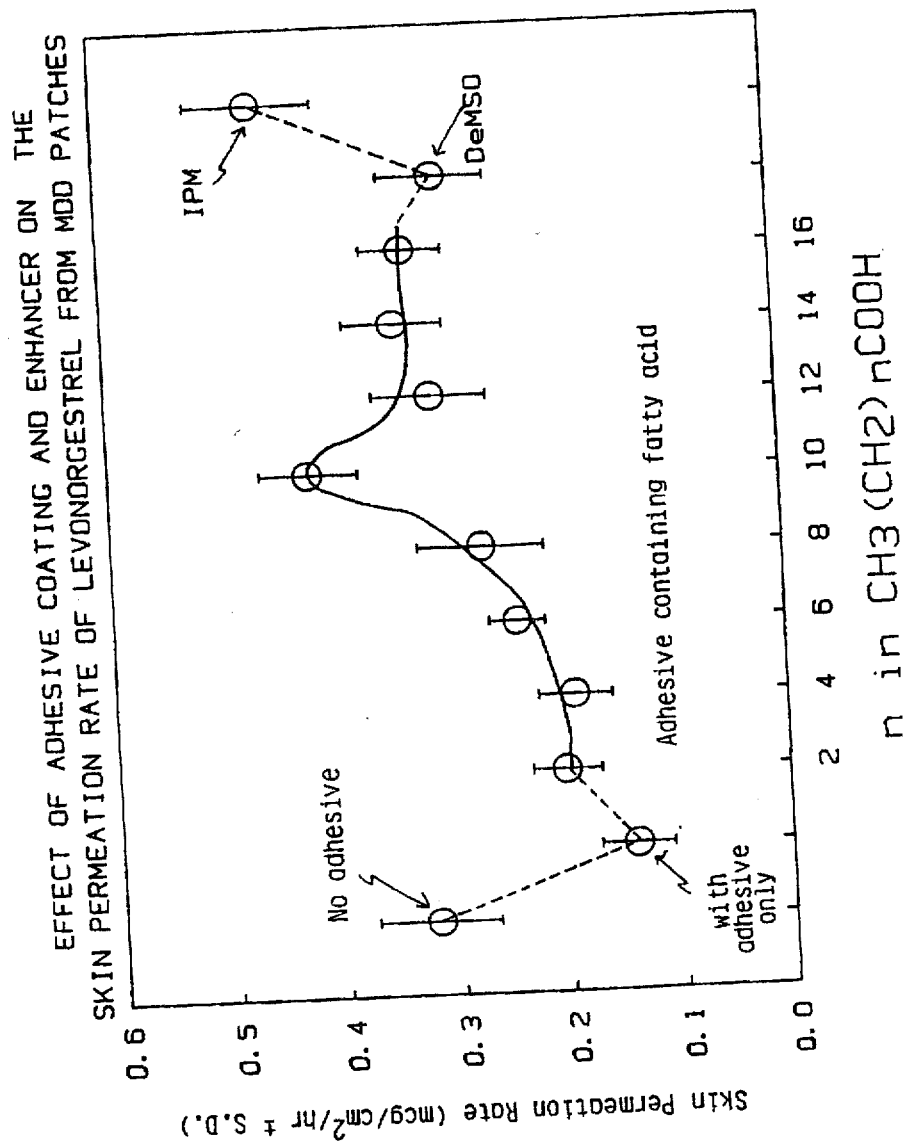
Figure 3:
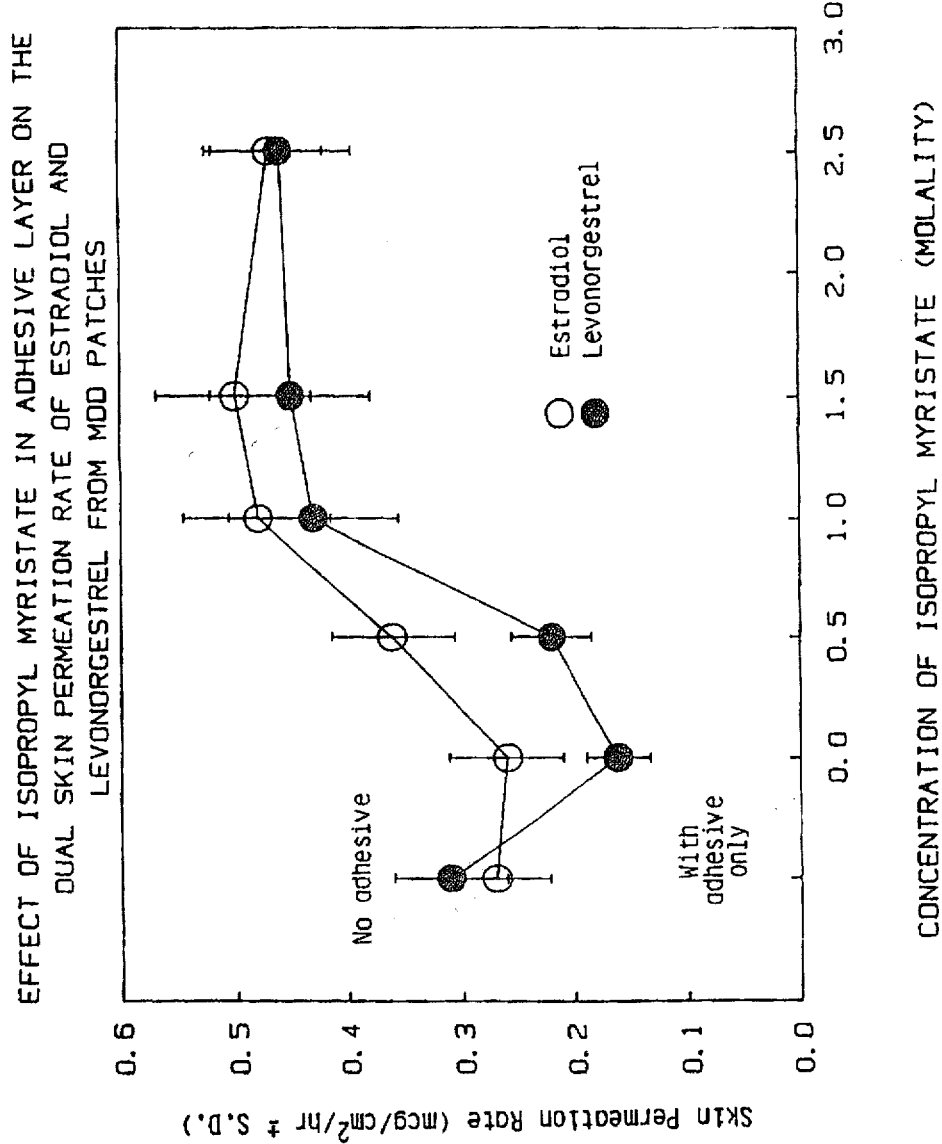
Figure 4:
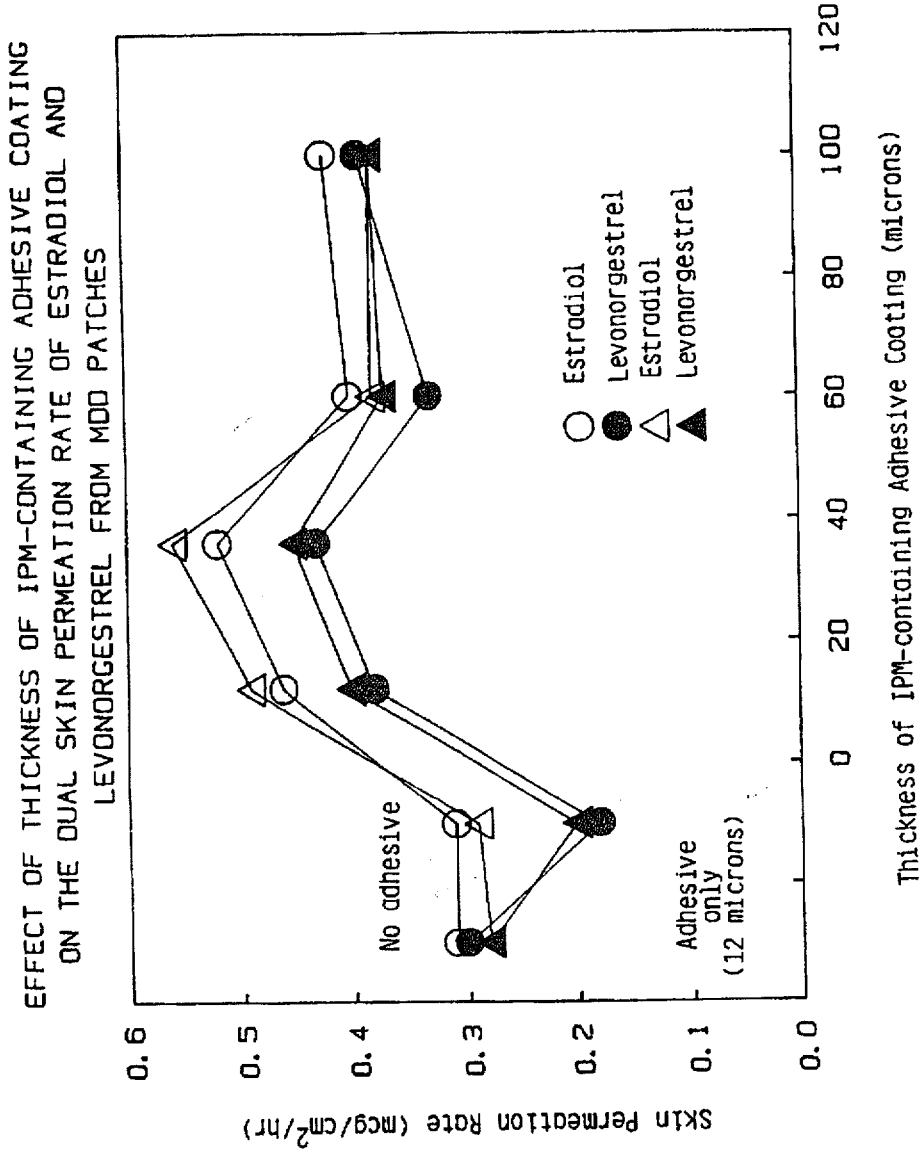

Transdermal polymer matrix dosage units (MD Patches) are obtained and evaluated as shown in the following Tables and FIGS. 1–4.

Effect of Isopropyl Myristate in Adhesive Layer on Skin Permeation and Lag Time Profiles[1] of Estradiol from MDD Patches Containing Estradiol and Levonorgestrel[2]

| Adhesive Composition[3] | Permeation Rate (mcg/cm$^2$/hr ± S.D.) | Lag Time (Hours ± S.D.) |
|---|---|---|
| (A) No Adhesive | 0.27 ± 0.048 | 14.5 ± 1.85 |
| (B) Adhesive Only | 0.26 ± 0.051 | 12.4 ± 1.10 |
| (C) Adhesive with IPM: | | |
| 0.5 M | 0.36 ± 0.054 | 19.8 ± 2.10 |
| 1.0 M | 0.48 ± 0.066 | 22.0 ± 2.92 |
| 1.5 M | 0.50 ± 0.069 | 18.9 ± 2.22 |
| 2.5 M | 0.47 ± 0.050 | 20.6 ± 2.79 |

[1] 14 Samples were taken during 90 hours of study.
[2] Fabricated from a formula which contains 5% (W/W) of levonorgestrel and 2.5% (W/W) of estradiol dispersed in separate microreservoir compartment (10% W/W) containing aqueous 40% (V/V) PEG 400 solution.
[3] Enhancer-incorporated adhesive coating layer is 16 microns thick.

Effect of Isopropyl Myristate in Adhesive Layer on Skin Permeation and Lag Time Profiles[1] of Levonorgestrel from MDD Patches Containing Estradiol and Levonorgestrel[2].

| Adhesive Composition[3] | Permeation Rate (mcg/cm$^2$/hr ± S.D.) | Lag Time (Hours ± S.D.) |
|---|---|---|
| (A) No Adhesive | 0.31 ± 0.049 | 32.5 ± 6.22 |
| (B) Adhesive Only | 0.16 ± 0.028 | 29.8 ± 3.45 |
| (C) Adhesive with IPM: | | |
| 0.5 M | 0.22 ± 0.037 | 28.9 ± 4.56 |
| 1.0 M | 0.43 ± 0.076 | 36.6 ± 7.01 |
| 1.5 M | 0.45 ± 0.072 | 33.2 ± 6.72 |
| 2.5 M | 0.46 ± 0.066 | 32.8 ± 6.60 |

[1] 14 samples were taken during 90 hours of study.
[2] Fabricated from a formula which contains 5% (W/W) of lovonorgestrel and 2.5% (W/W) of estradiol dispersed in separate microreservoir compartment (10% W/W) containing aqueous 40% (V/V) PEG 400 solution.
[3] Enhancer-incorporated adhesive coating layer is 16 microns thick.

Effect of Thickness of IPM-Containing Adhesive Coating on the Skin Permeation Rate Profile[1] of Estradiol from MDD Patches[2] Containing Estradiol and Levonorgestrel

| Adhesive Composition | | Permeation Rate (mcg/cm$^2$/hr ± S.D.) | % C.V. | Lag Time (Hours ± S.D.) | % C.V. |
|---|---|---|---|---|---|
| (A) No Adhesive | a | 0.31 ± 0.066 | 21.3 | 14.1 ± 2.94 | 20.9 |
| | b | 0.28 ± 0.068 | 24.3 | 11.8 ± 2.80 | 23.7 |
| (B) Adhesive Only | a | 0.31 ± 0.062 | 20.0 | 12.9 ± 2.70 | 20.9 |
| | b | 0.29 ± 0.050 | 17.2 | 12.1 ± 2.02 | 16.7 |
| (C) Adhesive + IPM[3] | | | | | |
| 12 microns | a | 0.46 ± 0.071 | 15.4 | 15.9 ± 2.87 | 18.2 |
| | b | 0.49 ± 0.089 | 18.2 | 16.8 ± 3.01 | 17.9 |
| 36 microns | a | 0.52 ± 0.089 | 17.1 | 16.8 ± 3.11 | 18.5 |
| | b | 0.56 ± 0.091 | 16.3 | 17.6 ± 2.77 | 15.7 |
| 60 microns | a | 0.40 ± 0.071 | 17.8 | 14.9 ± 2.98 | 20.0 |
| | b | 0.38 ± 0.066 | 17.5 | 15.2 ± 3.15 | 20.7 |
| 100 microns | a | 0.42 ± 0.086 | 20.5 | 15.8 ± 2.12 | 13.4 |
| | b | 0.38 ± 0.079 | 20.8 | 17.4 ± 3.02 | 17.4 |

[1] 14 samples were taken during 103 hours of study.
[2] Fabricated from a formula which contains 2.5% (W/W) of levonorgestrel and 1.0% (W/W) of estradiol dispersed in microreservoir (10% W/W) containing aqueous 40% (V/V) PEG solution.
a Drugs were dispersed in separate microreservoirs.
b Drugs were dispersed in the same microreservoir.
[3] Each 12-micron adhesive coating contains one molality of IPM.

Effect of Thickness of IPM-Containing Adhesive Coating on the Skin Permeation Rate Profile[1] of Levonorgestrel from MDD Patches[2] Containing Estradiol and Levonorgestrel

| Adhesive Composition | | Permeation Rate (mcg/cm$^2$/hr ± S.D.) | % C.V. | Lag Time (Hours ± S.D.) | % C.V. |
|---|---|---|---|---|---|
| (A) No Adhesive | a | 0.30 ± 0.054 | 18.0 | 33.6 ± 4.2 | 12.5 |
| | b | 0.28 ± 0.049 | 17.5 | 30.8 ± 4.9 | 15.9 |
| (B) Adhesive Only | a | 0.18 ± 0.039 | 21.7 | 30.8 ± 5.4 | 17.5 |
| | b | 0.20 ± 0.041 | 20.5 | 31.4 ± 5.8 | 18.5 |
| (C) Adhesive + IPM[3] | | | | | |
| 12 microns | a | 0.38 ± 0.061 | 16.1 | 35.4 ± 7.9 | 22.3 |
| | b | 0.40 ± 0.079 | 19.8 | 36.2 ± 7.1 | 19.6 |
| 36 microns | a | 0.43 ± 0.078 | 18.1 | 34.4 ± 7.0 | 20.3 |
| | b | 0.45 ± 0.088 | 19.6 | 32.6 ± 5.9 | 18.1 |
| 60 microns | a | 0.33 ± 0.054 | 16.4 | 30.8 ± 5.2 | 16.9 |
| | b | 0.37 ± 0.068 | 18.4 | 31.6 ± 4.9 | 15.5 |
| 100 microns | a | 0.39 ± 0.072 | 18.5 | 34.4 ± 7.1 | 20.6 |
| | b | 0.38 ± 0.082 | 21.6 | 35.6 ± 6.9 | 19.4 |

[1] 14 samples were taken during 103 hours of study.
[2] Fabricated from a formula which contains 2.5% (W/W) of levonorgestrel and 1.0% (W/W) of estradiol dispersed in microreservoir (10% W/W) containing aqueous 40% (V/V) PEG solution.
a Drugs were dispersed in separate microreservoirs.
b Drugs were dispersed in the same microreservoir.
[3] Each 12-micron adhesive coating contains one molality of IPM.

What is claimed is:

1. A transdermal fertility-controlling polymer matrix dosage unit comprising:
   (a) a backing layer which is substantially impervious to the fertility-controlling estrogen and progestin hormones to be delivered transdermally;
   (b) a polymer matrix disc layer which is adhered to said backing layer and which has microdispersed therein effective dosage amounts of fertility-controlling estrogen and progestin hormones said estrogen being selected from the group consisting of 17-beta estradiol, ethinyl estradiol and biocompatible derivatives thereof convertible to said estradiols, progestin being selected from the group consisting of levonorgestrel and norethindrone, said polymer being bioacceptable and permitting said hormones to be transmitted for transdermal absorption, said hormones being stable in said polymer matrix and being transdermally absorbed simultaneously to provide at least minimum effective daily doses of said hormones to effect fertility control; and
   (c) an adhesive means for securing the dosage unit for transdermal absorption to the subject treated.

2. A transdermal fertility-controlling polymer matrix dosage unit of claim 1 wherein said polymer matrix layer has dispersed therein an effective amount of one or more skin permeation enhancing agents.

3. A transdermal fertility-controlling dosage unit of claim 1 wherein the polymer matrix is a silicone polymer or copolymer.

4. A transdermal fertility-controlling polymer matrix dosage unit of claim 3 wherein the silicone polymer or copolymer is a methyl silicone polymer or copolymer or a methylvinyl silicone polymer or copolymer.

5. A. transdermal fertility-controlling polymer matrix dosage unit of claim 1 wherein the polymer matrix disc layer is a crosslinked polysiloxane polymer of the following formula:

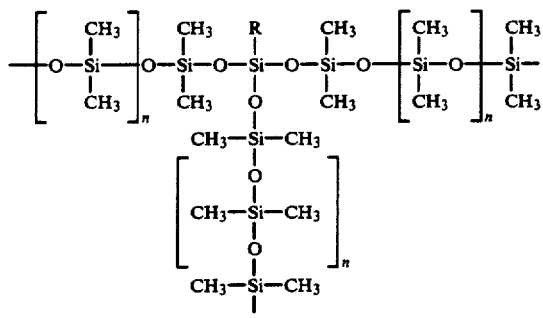

wherein R is selected from the group consisting of alkyl or alkoxy having 1–7 carbon atoms, vinyl, phenyl or a combination thereof; and wherein n is about 100 to about 5,000.

6. A transdermal fertility-controlling polymer matrix dosage unit of claim 3 wherein the matrix is made up of microdispersed compartments having a cross-sectional dimension of from about 10 to about 200 microns.

7. A transdermal fertility-controlling polymer matrix dosage unit of claim 1 wherein the estrogen hormone is 17-beta-estradiol.

8. A transdermal fertility-controlling polymer matrix dosage unit of claim 1 wherein the progestin is levonorgestrel.

9. A transdermal fertility-controlling polymer matrix dosage unit of claim 1 wherein the estrogen is 17-beta-estradiol and the progestin is levonorgestrel.

10. A transdermal fertility-controlling polymer matrix dosage unit of claim 1 wherein an effective progestin dosage of at least about 20 mcg per day is transdermally delivered for at least for a term of more than one day to about one week and an effective dose of estrogen of at least 20 is transdermally delivered for at least for a term of more than one day to about one week.

11. A transdermal fertility-controlling polymer matrix dosage unit of claim 10 wherein the progestin is levonorgestrel and the estrogen is 17beta-estradiol.

12. A transdermal fertility-controlling polymer matrix dosage unit of claim 6 wherein the progestin is levonorgestrel and the estrogen is 17-beta-estradiol.

13. A transdermal fertility-controlling polymer matrix dosage unit of claim 1 wherein the progestin is norethindrone and the estrogen is ethinyl estradiol.

14. A transdermal fertility-controlling polymer matrix dosage unit of claim 12 wherein the silicone polymer is a cross-linked siloxane polymer levonorgestrel is transdermally delivered at a dosage of at least about 20 mcg per day for at least for a term of more than one day to about one week and 17-beta-estradiol is transdermally delivered at a dosage of at least about 20 mcg per day for at least for a term of more than one day to about one week, the microdispersed compartment having present aqueous polyethylene glycol dispersing agent and the matrix layer having present an enhancing amount of a skin permeation enhancing agent.

15. A transdermal fertility-controlling polymer matrix dosoage unit of claim 12 wherein the silicone polymer is a cross-linked siloxane polymer norethindrone, is transdermally delivered at an effective dose for at least for a term of more than one day to about one week and ethinyl estradiol is transdermally delivered at an effective dialy dose for at least for a term of more than one day to about one week, the microdispersed compartment having present aqueous polyethylene glycol dispersing agent and the matrix layer having present an enhancing amount of a skin permeation enhancing agent.

16. A transdermal fertility-controlling polymer matrix dosage unit of claim 13 wherein the daily dose amounts are transdermally delivered for at least one week.

17. A transdermal fertility-controlling polymer matrix dosage unit of claim 14 wherein the cross-linked silicone polymer is polydimethylsiloxane.

18. A transdermal fertility-controlling polymer matrix dosage unit of claim 4 wherein the cross-linked silicone polymer is a cross-linked methylvinyl silicone polymer.

19. A transdermal fertility-controlling polymer matrix dosage unit of claim 5 wherein the skin permeation enhancing agent is present in the matrix layer, the adhesive layer or both layers and is selected from isopropyl myristate, straight chain fatty acids having an alkyl groups having 4 to 18 carbon atoms or decyl methyl sulfoxide.

20. A transdermal fertility dosage unit of claim 16 wherein the skin permeation enhancing agent is present in the matrix layer, the adhesive layer or both layers and is selected from isopropyl myristate, straight chain fatty acids having an alkyl groups having 4 to 18 carbon atoms or decyl methyl sulfoxide.

21. A process of controlling fertility by applying to the skin of a subject desiring said treatment a dosage unit as described in claim 1 to provide at least the minimum effective dose amounts of progestin and estrogen for about the first three weeks of a menstrual cycle for successive menstrual cycles for a peroid extending as long as fertility control is desired.

22. A process of claim 19 wherein the dosage unit used is as described in claim 3.

23. A process of claim 19 wherein the dosage unit used is as described in claim 4.

24. A process of claim 19 wherein the dosage unit used is as described in claim 6.

25. A process of claim 19 wherein the dosage unit used is as described in claim 7.

26. A process of claim 19 wherein the dosage unit used is as described in claim 10.

27. A process of claim 19 wherein the dosage unit used is as described in claim 11.

28. A process of claim 19 wherein the dosage unit used is as described in claim 12.

29. A process of claim 19 wherein the dosage unit used is as described in claim 17.

30. A process of claim 19 wherein the dosage unit used is as described in claim 18.

* * * * *